(12) United States Patent
Frohn

(10) Patent No.: US 6,447,492 B1
(45) Date of Patent: Sep. 10, 2002

(54) DIALYSIS DRAINAGE STAND

(76) Inventor: Nancy B. Frohn, P. O. Box 2285, Oxford, MS (US) 38655

( * ) Notice: Subject to any disclaimer, the term of this patent is extended or adjusted under 35 U.S.C. 154(b) by 0 days.

(21) Appl. No.: 09/425,268

(22) Filed: Oct. 22, 1999

Related U.S. Application Data

(60) Provisional application No. 60/108,978, filed on Nov. 18, 1998.

(51) Int. Cl.$^7$ .................................................. A61M 1/00
(52) U.S. Cl. ........................................ 604/322; 600/580
(58) Field of Search ................................ 604/322, 317, 604/28, 29; 600/573, 580, 584, 249

(56) References Cited

U.S. PATENT DOCUMENTS

| | | | |
|---|---|---|---|
| 4,295,619 A | | 10/1981 | Kulin et al. |
| 4,393,880 A | | 7/1983 | Taylor |
| 4,403,992 A | | 9/1983 | Bertellini et al. |
| 4,447,939 A | | 5/1984 | Taylor |
| 4,654,298 A | * | 3/1987 | Babb et al. ................ 435/18 |
| 4,712,567 A | | 12/1987 | Gille et al. |
| 5,141,492 A | | 8/1992 | Dadson |
| 5,693,039 A | | 12/1997 | Stewart et al. |
| 5,720,741 A | | 2/1998 | Stewart et al. |
| 5,722,947 A | | 3/1998 | Jeppsson et al. |
| 5,782,796 A | * | 7/1998 | Din et al. ................ 604/27 |

FOREIGN PATENT DOCUMENTS

WO PCT/US83/01632 10/1983

* cited by examiner

*Primary Examiner*—Brian L. Casler
*Assistant Examiner*—Mark Han

(57) ABSTRACT

A device is shown for displaying drainage on a ramp from a body cavity into a bag. This device is designed to allow an individual seated at rest to view the bag while it steadily fills with fluid. The ramp may be back lit with writing on it so that evidence of infection is visible. The bag may contain a flow disturbing surface and a dye in order to make the presence of infection more visible.

25 Claims, 3 Drawing Sheets

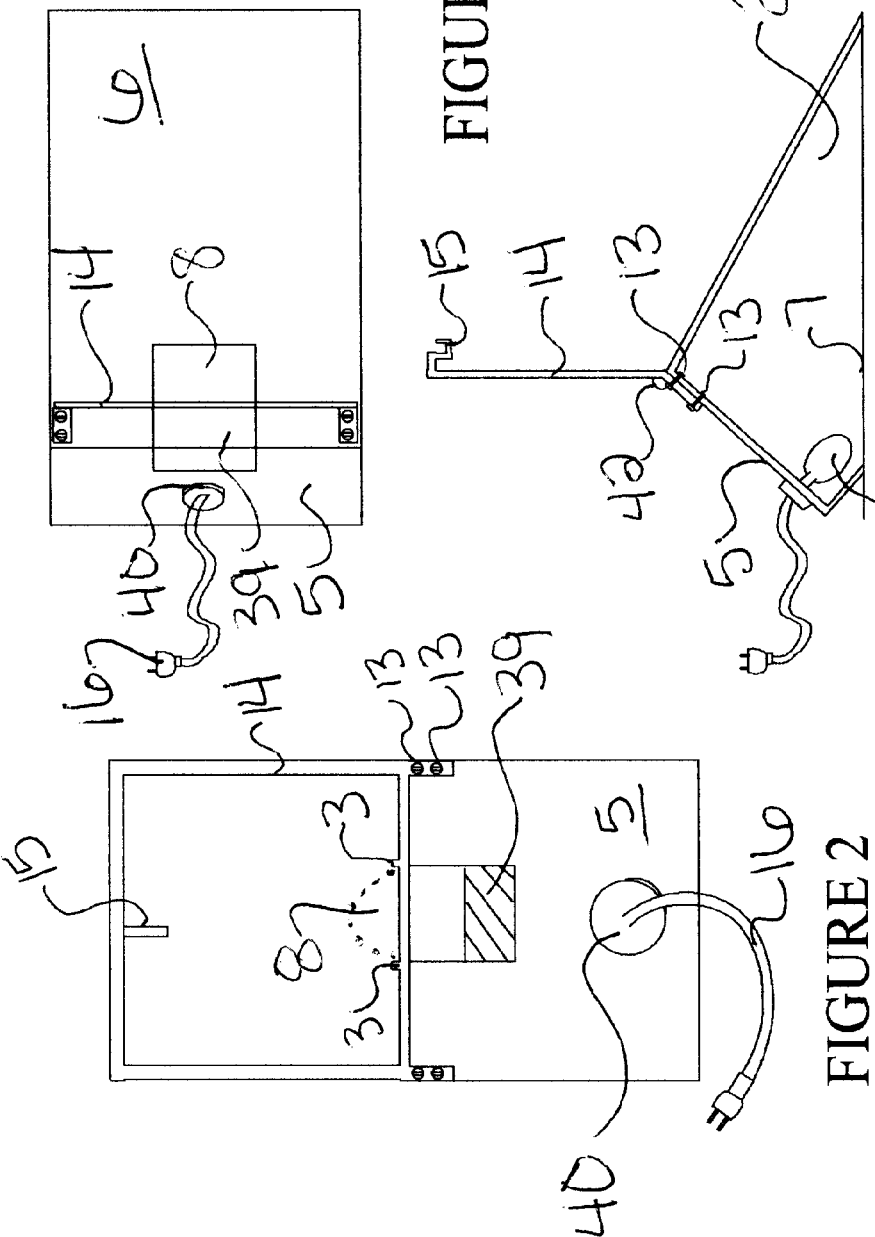

DIALYSIS DRAINAGE STAND

PRIORITY STATEMENT

This application is a continuation in part of provisional patent application No.: 60/108,978 Filed: Nov. 10, 1998.

BACKGROUND OF INVENTION

1. Field of Invention

The invention relates to peritoneal dialysis. More particularly, the invention relates to stands for holding dialysis bags and methods for determining completion of peritoneal drainage during dialysis and methods for testing for the presence of infection during peritoneal dialysis.

2. Prior Art

Dialysis drainage bags are known in the prior art.

3. General Discussion of the Invention

Peritoneal Dialysis is a technique by which a glucose solution is inserted into the abdominal or peritoneal cavity of the user. This is particularly necessary for people whose kidneys have stopped functioning in order to properly cleanse the blood and this is a typical complication for diabetes.

A glucose solution within the peritoneal cavity tends to function much as the kidney does for performing dialysis on the blood. In order to accomplish this result an opening into the peritoneal cavity is surgically prepared and a fixture is inserted into the abdominal wall connecting the abdominal wall to the outside environment so that a dialysis tube may be inserted into that fixture. The insertable dialysis tube is in turn connected to a three way valve. The user typically connects this while in a sitting position. One end of the three way valve goes above the user to a glucose solution which is suspended above the user so that gravity will allow the glucose solution to drain into the abdominal cavity. The other end of the three way valve goes to a dialysis bag which in the past has lain on the ground and fills with the drained solution.

This drainage bag fills slowly with the used glucose solution from the users peritoneal cavity, but it is often difficult to tell when the bag is filled and when the drainage is completed.

The present invention seeks to address this problem and also addresses the problem of infection which can often accompany this procedure.

The present invention is also designed in order to make the procedure more comfortable. The procedure must also be performed several times a day. It is very important that the procedure be as comfortable as possible for the patient who is typically carrying out the procedure independently and seated.

In order to accomplish this result, the invention has a slanting surface which supports the drainage bag which is in front of the face of the user on the ground. In this way the user who is sitting on a chair can look down at the slanted surface and see it clearly.

The slanting face provides an opening at the point where the dialysis tubing enters the drainage bag and this opening is illuminated by either a reflected light source or a light source held below the point at which the opening in the slanting face is present.

By illuminating the area from behind where the tubing enters the dialysis bag the stream of fluid entering the dialysis bag is easily observed.

The existing dialysis bags are designed to be hung from hooks and therefore have two holes at the top of the dialysis draining bag. At the top of the slanting face, posts are provided which go into the openings in order to support the dialysis bag in the appropriate location with a point at which the tube enters the dialysis bag being over the opening in the face so that the drainage may be easily observed. In this way it is fairly obvious to the user when the drainage is complete.

Another feature of the present invention which is also accomplished by having the slanting surface is that the face of the surface on which the dialysis bag rests is a bright surface usually white in color with colored writing which is easily discernable if the bag and fluid is clear. The dialysis bag is partially opaque until it begins to fill with dialysis fluid and then it becomes clear. In this way the letters on the face of the slanting surface become easily readable as the bag is filled. However, if there is a presence of infection, then cloudiness associated within the infection is notable either against the white surface or against the lettering. This indicates to the user that he needs to be checked in order to see if there is infection present. Because this procedure involves contact between the outside environment and the peritoneal cavity, and the insertions of fluid from the outside environment into the peritoneal cavity, there is a high probability of infection, and infections are relatively common. This method of early detection is critical in order to minimize the use of antibiotics and in order to prevent the infection from growing to the level where they cause discomfort or even cause a termination of the peritoneal dialysis procedure.

Once an indication occurs, the patients either have a more sensitive test or the patient can have the dialysis fluids tested in order to see whether an infection is present and if necessary, begin to take an antibiotic regimen.

Because the dialysis tubing comes from the abdomen of the user where the fixture penetrates the skin, any pulling on the dialysis tubing can create a great deal of discomfort to the user.

Another improvement present in the present invention is a dialysis tubing holder which supports the tubing above the slanting surface. This not only makes the drainage into dialysis bag more clear but is also provides for the tubing to be supported in a position in the proper location before it is inserted into the individual and it also supports at a height above the level of the bag so that the possibility of the individual pulling on the tubing as he sits through the dialysis procedure is greatly reduced.

Additionally, a weighing mechanism may be incorporated into the stand so that the user need not lift the bag to weigh it and so that the user may also determine when the bag has been adequately filled or approximately when bag has been filled.

It is therefore an object to the invention to provide a method of identifying when drainage is complete to a user of peritoneal dialysis.

It is a further object of the invention to provide a procedure for determining whether infection is present in a glucose solution which is obtained during the peritoneal dialysis procedure.

It is a further object of the invention to add to the comfort of the individual viewing the drainage of the peritoneal dialysis procedure as well as to provide enhanced comfort to the individual when the peritoneal dialysis tubing is inserted into the fixture into the user's peritoneal cavity.

It is a further object of this invention to allow the user to have his dialysis bag weighed without effort.

These and other objects and advantages of the invention will become better understood hereinafter from a consideration of the specification with reference to the accompanying drawings forming part thereof, and in which like numerals correspond to parts throughout the several views of the invention.

BRIEF DESCRIPTION OF THE DRAWINGS

For a further understanding of the nature and objects of the present invention, reference should be made to the following detailed description taken in conjunction with the accompanying drawings in which like parts are given like reference numerals and wherein:

FIG. 1 is a top view of the invention.

FIG. 2 is a back view.

FIG. 3 is a side view.

DETAILED DESCRIPTION OF THE PREFERRED EXEMPLARY EMBODIMENTS

The invention is best understood as being a dialysis stand for a dialysis bag which aids in the observation of the drainage and clarity of the effluent.

Figure 4:
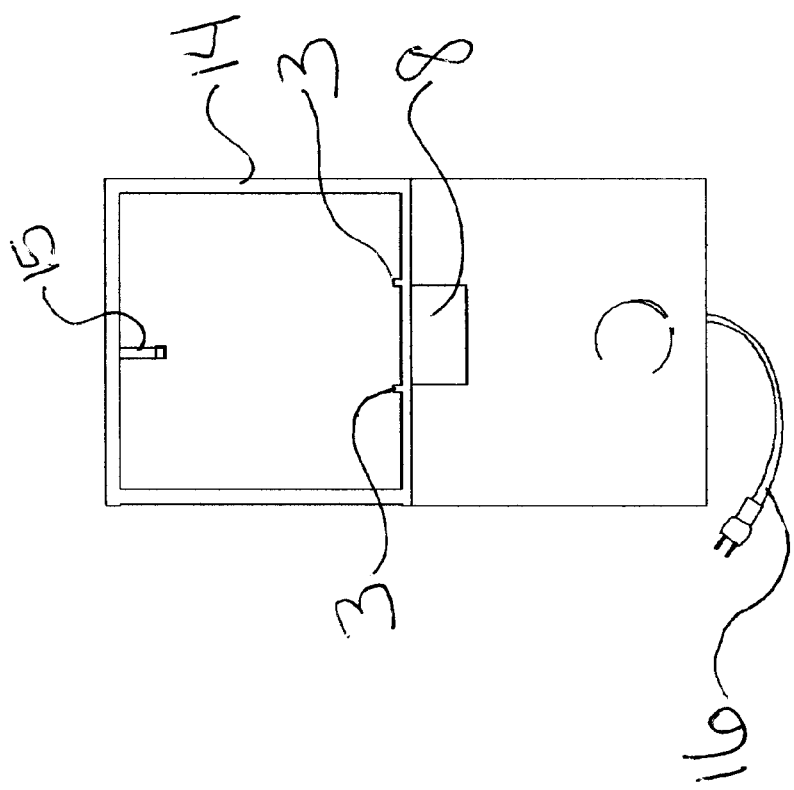
FIG. 4 is a front view.
Figure 5:
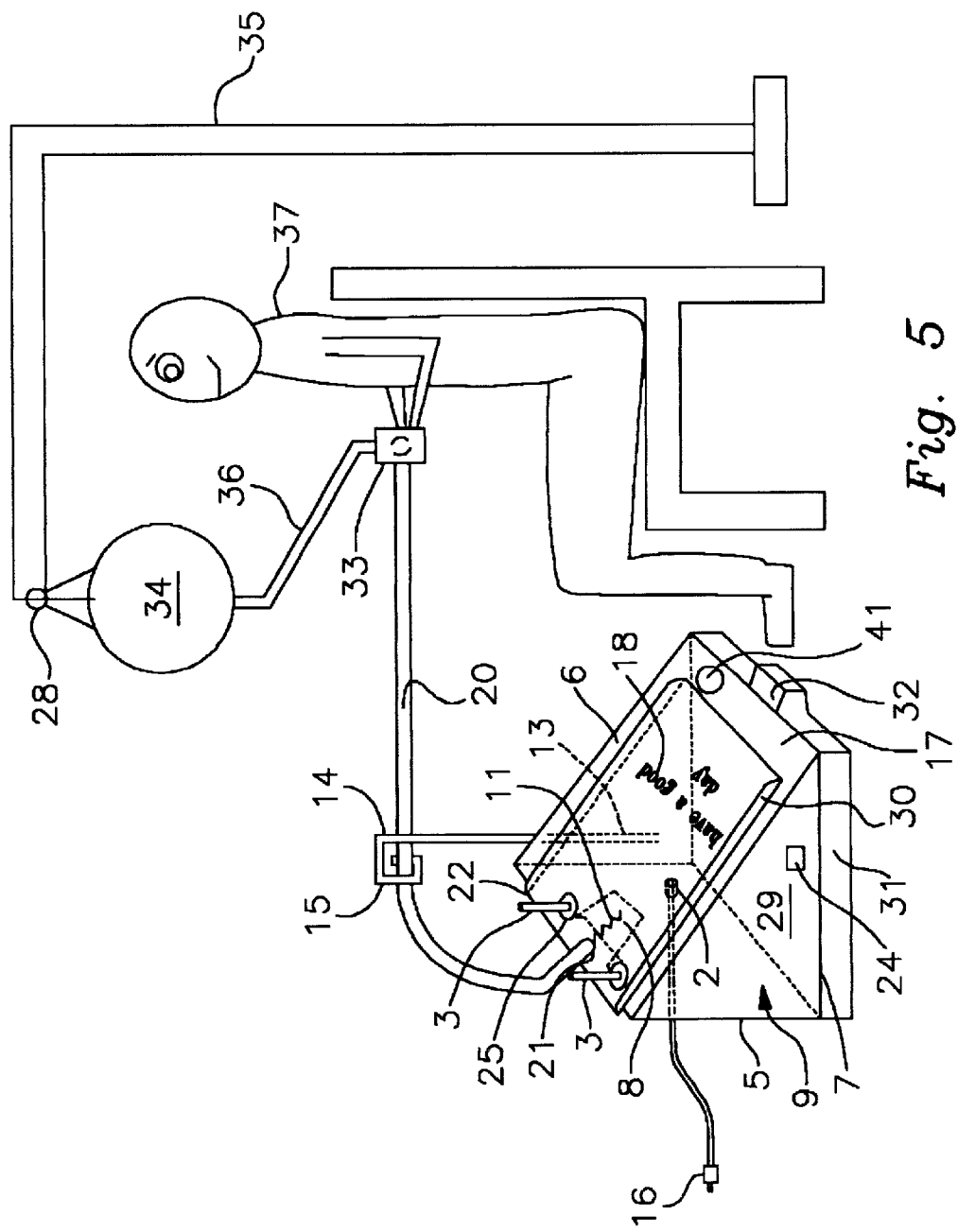
FIG. 5 is a perspective view which shows the invention as it is used.

As can best be seen by reference to FIG. 5, the function of the invention is to support a clear plastic bag 30 having a bag top 22 and a bag bottom 23. The bag top 22 defines bag holes 25 which can fit into posts 3 mounted near the top of the slanting plate 6. The slanting plate 6 is held at the appropriate angle by a vertical support 5 and may also have a base 7 connecting the slanting support to the vertical support in order to provide more amount of support.

A light opening 8 is defined in the middle, slanting support near the top and in the middle near the top of the vertical support so that light from a light source, such as bulb 2, may pass through in order to illuminate the bag top 22 where the dialysis tubing 20 enters the bag 30 at entrance 21. These light openings may be actual openings or clear areas to allow illumination.

The slanting plate 6 has a slanting face 17 which is preferably a bright color such as white and has writing 18 on the face in a color such as light blue in order to allow observation of the letters through the dialysis solution as either being clear or cloudy in order to assist in determining whether infection is present.

The light may be fluorescent or another light type source in order to better illuminate or fluorescence infection and in order to maintain a low temperature in the bag 30 and slanting surface 6. The light source is shown as a bulb 2, but may also be a reflecting mirror or any other source of illumination.

The light may also illuminate the letters 18 through a semi-transparent area in the slanting face 17 in order to back-light the letters 18 to better indicate the presence or absence of infection.

A three way valve 33 is shown in FIG. 5 which allows, selectively, fluid from a feed tube 36 from a fluid bag 34 supported on a stand 35 above the abdomen of the user 37 or to the drainage tube 20 so that the user may, through the use of this valve allow fluid to be received into the abdomen or drained into the bag 30. The fluid bag 34 may hang from a scale 28 so that the weight of the fluid may be measured against the weight on the drainage bag.

The slant angle of 26 of the slanting face 17 may be controllable by the user or it may be fixed. As shown in FIG. 3, it is preferably approximately 30 degrees if fixed.

The illumination of the light 2 in conjunction with the light opening 8 is in order to make it easier for a person who is utilizing the dialysis support 1 to monitor his drainage and check for the presence of infection. A clock or timer 41 may be added to further assist in approximating timing of the drainage. Typically the user would be sitting, facing the slanting plate.

A hook attachment 13 on to the side wall 29 or other location (FIG. 5 shows a side wall 29 attachment) serves to hold a hook arm 14 which ends in a hook 15 which may hold the dialysis tubing 20 in order to prevent an uncomfortable amount of pulling on the tubing and in order to hold it up so that it is easier to put in place without pulling. In the preferred embodiment, this hook 15 holds the tubing 20 approximately parallel to or slightly below the point where the tubing 20 enters the user's abdomen. This location limits pulling two ways. First, it supports the tube slightly below the point of entry. Second, it keeps the bag 30 from tugging on the tubing 20 where it enters the body as the bag 30 fills.

The light source, here bulb 2, may be protected within the slanting plate 6, vertical support 5, and side walls 29. Ventilation is provided by openings 38 and 39 as shown in FIG. 2 or by ventilation within the side walls 29. A fan 24 may also be provided to circulate the air. A reflective mirror reflecting sun-light or another bulb would be one form of an alternate light source.

The hook 15 in the preferred embodiment holds the tubing 20 loosely. It may have a clamp to clamp the tubing 20 in place if desired.

A process for dialysis drainage is thereby described which may be summarized as a method for peritoneal dialysis from the peritoneal cavity comprising the steps of:

1) Draining a solution from a peritoneal cavity into a tube;
2) setting a clear container, here a dialysis bag 30 having a top 22 and a bottom 23 at an angle 26 where it may be viewed by the user;
3) emptying the tube 20 into the top 22 of the bag 30;
4) illuminating the bag top 22 so that the flow of solution into the container may be viewed so that when the flow ceases, a viewer knows that the draining is completed.

The step of setting a clear: container having a top and a bottom where it may be viewed may further comprise the steps of.

5) placing the clear bag 30 on a plate 6 facing the user; and
6) providing a picture or writing 18 on the plate 6 so that the writing 18 may be viewed through the clear bag 30 as liquid fills the container to determine the presence of infection.

The process may be alternatively defined by the following steps:

1) supporting a dialysis bag 30 at an angle of between 20 and 80 degrees to a sitting surface (the preferred angle shown in FIG. 3 shows an angle of 30 degrees;
2) illuminating the area of the bag where dialysis tubing 20 enters the bag 30;
3) displaying a written message or picture below the bag 30 so that the letters may be viewed to distinguish the clarity of the fluid within the bag 30.
4) providing a timer 41 or scale 31 with a buzzer or display 32 which notifies the user at the estimated time of completion.

Additional steps in this process may include: (4) displaying the weight of the bag as it fills with or without a signal (light or buzzer) when it reaches a pre-set weight, (5) illuminating a semi-transparent slanting face 17 from behind or from in front of the bag 30, (6) creating turbulence at the point where the tubing 20 enters the bag 30, (7) supporting the dialysis tubing 20 at approximately the level of the entry to the user's abdomen, (8) coloring the fluid to enhance the appearance of flow or to indicate the presence of infection and (9) providing a three way valve for selectively allowing dialysis fluid into the user's abdomen and allowing drainage from the abdomen to the drainage bag 30.

Additional steps, as indicated above, could include: creating turbulence at the top of the container to further show the flow of the drainage; dying the solution for the purpose of indicating flow within the dialysis or and dying the solution for the purpose of indicating the presence of infection within the dialysis bag.

Turbulence causing ridges 11 are shown in FIG. 1 for this purpose. The ridges 11 may be made of dying agents. The dying agents may alternatively be inside of the tubing. The purpose of the dying agents would be to color the fluid so that the flow could be more easily detected. For example, if the ridges 11 were made of dye and were gradually released, the flow of color downward as the bag 30 is filled would allow the user to closely monitor the drainage. Alternatively, or additionally, the dye could be made to react with infection agents (bacteria) to display a particular color or clarity when infection (bacteria) was present in a sufficient quantity.

A scale 31 having a display 32 may be incorporated into the invention so that the weight of the bag may be tracked as it is filled and after it is filled. This serves two purposes. One purpose is to approximate the finish time. The scale 31 may have a speaker, as part of the display 32, to verbally announce the weight or the point at which the bag 30 is approximately full or may have a written display 32 to indicate the weight or percentage of completion. This also is used to weigh the bags of fluid which may otherwise have to be separately weighed. A second scale 28 may be provided to weigh the fluid bag which drains into the peritoneal cavity so that the amount of fluid entering may be determined.

FIG. 2 shows an alternative version which provides ventilation through bottom slot 38 and back slot 39. The back slot 39 may be continuous with light opening 8 which may be a transparent area or an actual opening. A continuous opening is desired to add ventilation to the interior defined by the invention. Also as shown in FIG. 2, the posts 3 may be continuously molded with the hook arm 14 and hook 15. FIG. 2 also shows the receptacle 40 for the light 8 mounted between the bottom slot 38 and the back slot 39. The power cord 16, powers the receptacle 40.

The angle 26 of the slanting face 6 is shown in FIG. 3 as 30 degrees. FIG. 3 also shows the angle 42 at which the hook arm 14 rises from the vertical support 5 where it is attached so that it is approximately perpendicular to the surface on which the invention rests.

FIG. 1 shows a top view of the alternative version of the invention shown in FIG. 2. Here the securing screws 27 hold the posts 3 and hook arm 14 in place against the vertical support 5 on either side of where the bag 30 sits. FIG. 1 also shows the light opening 8 and back slot 39 to be continuous except where the hook arm 14 runs across.

The specific approximate measurements as shown in FIGS. 1–4 of the preferred embodiment would yield a length of the plate 6 of fourteen (14) inches from top to bottom and a width of eight and seven eighth (8⅞th) inches. There is a thirty-seven (37) degree angle from the base 7 to a seven and a half (7½) inch support 5. The elevation is eighteen (18) inches for the hook arm 14. The light opening 8 is two and three sixteenths (2 3/16) inches by three and one sixteenth (3 1/16) inches. The base is approximately fourteen and a half(14½) inches long.

Because many varying and different embodiments may be made within the scope of the inventive concept herein taught and because many modifications may be made in the embodiment(s) herein detailed in accordance with the descriptive requirements of the law, it is to be understood that the details herein are to be interpreted as illustrative and not in a limiting sense.

What is claimed is:

1. A support for holding a drainage bag above a surface where the drainage bag has a bottom and a top, said top defining a tube entrance for receiving a dialysis tube at an opening in the top of the bag for use with peritoneal dialysis where a dialysis insertion site into the patient is present, comprising: a slanting plate having a plate bottom and a plate top and a length between the plate top and the plate bottom, said plate having a front and rear and where. the plate top is higher relative to the surface than the plate bottom so that the slanting plate slants downward from the plate top to the plate bottom; and a bag holding means for holding the bag top near the plate top so that the bag top is higher than the bag bottom and wherein the slanting plate is light permeable at the tube entrance and further comprising a light source located below the slanting plate.

2. The invention of claim 1 wherein the bag top defines post holes and wherein the bag holding means comprises posts rising above the plate which fits within the post holes.

3. The invention of claim 1 wherein the bag holding means comprises at least one clip attached to the top of the plate for holding the bag top to the plate.

4. The invention of claim 1 wherein the light source is a fluorescent light.

5. The invention of claim 1 further comprising a coloring means within the tube for coloring the liquid as it flows into the bag so that the flows is more visible.

6. The invention of claim 1 further comprising a coloring means within the bag for coloring the liquid as it flows into the bag so that the flow is more visible.

7. The invention of claim 1 further comprising a coloring means within the bag for displaying a visual indication when infection is present.

8. The invention of claim 1 further comprising a support stand held above the slanting plate and approximately over the tube entrance having a tube receiving means for holding the tube to reduce pulling on the tube where it enters the abdomen as the bag is moved or filled.

9. The invention of claim 8 wherein the support stand tube receiving means further comprises a tube receiving means for holding the tube below the dialysis insertion into the patient.

10. The invention of claim 9 wherein the tube receiving means comprises a clip for releasably holding the tube below the dialysis insertion site into the patient, but above the tube entrance into the dialysis bag.

11. The invention of claim 10 wherein the support stand is attached to the slanting face.

12. The invention of claim 2 wherein the slanting plate further comprises at least two supporting walls holding the slanting plate above the surface and where the light source is contained within at least two supporting walls.

13. The invention of claim 12 wherein one of the at least two supporting walls supports the light source and wherein the at least two supporting walls describe ventilation openings to ventilate the light source.

14. The invention of claim 1 further comprising a fill indicator means for indicating when the bag is approximately filled.

15. The invention of claim 14 wherein the fill indicator means is a scale on which the bag rests above the floor.

16. A support for holding a drainage bag above a surface where the drainage bag has a bottom and a top, said top defining a tube entrance for receiving a dialysis tube at an opening in the top of the bag for use with peritoneal dialysis where a dialysis insertion site into the patient is present, comprising: a slanting plate having a plate bottom and a plate top and a length between the plate top and the plate bottom, said plate having a front and rear and where the plate top is higher relative to the surface than the plate bottom so that the slanting plate slants downward from the plate top to. the plate bottom ;and a bag holding means for holding the bag top near the plate top so that the bag top is higher than the bag bottom and wherein the slanting plate defines an opening at the tube entrance and further comprising a light source below the slanting plate.

17. A support for holding a drainage bag above a surface where the drainage bag has a bottom and a top, said top defining a tube entrance for receiving a dialysis tube at an opening in the top of the bag for use with peritoneal dialysis where a dialysis insertion site into the patient is present, comprising: a slanting plate having a plate bottom and a plate top and a length between the plate top and the plate bottom, said plate having a front and rear and where the plate top is higher relative to the surface than the plate bottom so that the slanting plate slants downward from the plate top to the plate bottom, and a bag holding means for holding the bag top near the plate top so that the bag top is higher than the bag bottom and where the bag is clear and where the plate front further comprises writing so that the clarity of the writing seen through the bag indicates the absence of infection.

18. A support for holding a drainage bag above a surface where the drainage bag has a bottom and a top, said top defining a tube entrance for receiving a dialysis tube at an opening in the top of the bag for use with peritoneal dialysis where a dialysis insertion site into the patient is present, comprising: a slanting plate having a plate bottom and a plate top and a length between the plate top and the plate bottom, said plate having a front and real and where the plate top is higher relative to the surface than the plate bottom so that the slanting plate slants downward from the plate top to the plate bottom, and a bag holding means for holding the bag top near the plate top so that the bag top is higher than the bag bottom and further comprising at least one ridge at the tube entrance to create turbulence so that the flow is more visible.

19. A method for peritoneal dialysis from the peritoneal cavity comprising the steps of:
   a. draining a solution from the peritoneal cavity into a tube;
   b. setting a clear container having a top and a bottom where it may be viewed by the user;
   c. emptying the tube into the .top of the container;
   d. illuminating the container top so that the flow of solution into the container may be viewed so that when the flow ceases, the user knows that the draining is completed.

20. The method of claim 19 wherein the step of setting a clear container having a top and a bottom where it may be viewed further comprises the steps of:
   of placing the clear container on a slanting plate facing the user.

21. The method of claim 20 further comprising the step of:
   writing on the slanting face so that the writing may be vie ed through the clear container as liquid fills the container by the user to determine the presence of infection.

22. The method of claim 20 further comprising the step of creating turbulence at the top of the container to further show the flow of the drainage.

23. The method of claim 19 further comprising the step of dyeing the solution to enhance visibility of the turbulence associated with the flow into the container.

24. The method of claim 19 further comprising the step of dyeing the solution for the purpose of indicating the presence of infection within the container.

25. The method of claim 19 further comprising the step of indicating to the user when the bag is approximately filled by displaying the weight of the bag as it is filled.

* * * * *